US009663372B2

(12) United States Patent
Gogotsi et al.

(10) Patent No.: US 9,663,372 B2
(45) Date of Patent: May 30, 2017

(54) DISAGGREGATION OF AGGREGATED NANODIAMOND CLUSTERS

(75) Inventors: Yury Gogotsi, Warminster, PA (US); Vadym Mochalin, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 769 days.

(21) Appl. No.: 14/117,652

(22) PCT Filed: May 7, 2012

(86) PCT No.: PCT/US2012/036741
§ 371 (c)(1),
(2), (4) Date: Feb. 11, 2014

(87) PCT Pub. No.: WO2012/158380
PCT Pub. Date: Nov. 22, 2012

(65) Prior Publication Data
US 2015/0038593 A1    Feb. 5, 2015

Related U.S. Application Data

(60) Provisional application No. 61/486,513, filed on May 16, 2011.

(51) Int. Cl.
| | |
|---|---|
| *B02C 23/00* | (2006.01) |
| *C01B 31/06* | (2006.01) |
| *A61K 47/02* | (2006.01) |
| *B02C 23/06* | (2006.01) |
| *B02C 23/08* | (2006.01) |
| *B02C 23/18* | (2006.01) |

(Continued)

(52) U.S. Cl.
CPC ............ *C01B 31/065* (2013.01); *A61K 47/02* (2013.01); *B02C 23/06* (2013.01); *B02C 23/08* (2013.01); *B02C 23/18* (2013.01); *C09K 5/14* (2013.01); *H01B 1/04* (2013.01)

(58) Field of Classification Search
CPC ........ B02C 23/00; B02C 23/08; B02C 17/186
USPC .......................................................... 241/30
See application file for complete search history.

(56) References Cited

U.S. PATENT DOCUMENTS

| 5,876,759 A | 3/1999 | Gowan et al. |
| 6,520,837 B2 | 2/2003 | Weichert |

(Continued)

FOREIGN PATENT DOCUMENTS

| WO | WO 2009/060613 A1 | 5/2009 |
| WO | WO 2010/121323 A1 | 10/2010 |
| WO | WO 2012/158380 A1 | 11/2012 |

OTHER PUBLICATIONS

Pentecost et al, "Deaggregation of Nanodiamond Powders Using Salt- and Sugar-Assisted Milling", Applied Materials & Interfaces, 2010, 2(11), 3289-3294, Published Online: Nov. 2, 2010.

(Continued)

*Primary Examiner* — Faye Francis
(74) *Attorney, Agent, or Firm* — Baker & Hostetler LLP

(57) ABSTRACT

The present invention is directed to methods of disaggregating nanodiamond clusters, especially those clusters typically produced from detonation syntheses, the nanodiamond particles and dispersions produced from these disaggregation processes, and compositions derived from these nanodiamond particles and dispersions.

30 Claims, 7 Drawing Sheets

(51) Int. Cl.
*C09K 5/14* (2006.01)
*H01B 1/04* (2006.01)

(56) References Cited

U.S. PATENT DOCUMENTS

| | | |
|---|---|---|
| 7,758,689 B2 | 7/2010 | Li et al. |
| 2003/0234304 A1 | 12/2003 | Miao |
| 2010/0092563 A1 | 4/2010 | Raffaele et al. |
| 2010/0305309 A1 | 12/2010 | Ho et al. |
| 2011/0172132 A1 | 7/2011 | Branson et al. |
| 2011/0252713 A1* | 10/2011 | Chakraborty ............ B01J 3/062 51/298 |

OTHER PUBLICATIONS

International Application No. PCT/US12/36741: International Search Report and Written Opinion dated Aug. 13, 2012, 10 pages.
Krüger et al, "Unusually Tight Aggregation in Detonation 3 Nanodiamond: Identification and Disintegration", Carbon, Mar. 2, 2005, 43, 1722-1730.
Xu, K. and Xue,Q., "A New Method for Deaggregation of Nanodiamond From Explosive Detonation: Graphitization-Oxidation Method", 2004, 46, 633-634.
Xu et al, "Influence of Surface Modification Adopting Thermal Treatments on Dispersion of Detonation Nanodiamond", Mar. 2005, 178(3), 688-693.
Pichot et al, "An Efficient Purification Method for Detonation Nanodiamonds", Jan. 2008, 17(1), 13-22.
Osswald et al, "Control of sp2/sp3 Carbon Ratio and Surface Chemistry of Nanodiamond Powders by Selective Oxidation in Air", J. Am. Chem. Soc., Aug. 16, 2006, 128 (35), 11635-11642.
Vul et al, "Direct Observation of Isolated Ultrananodimensional Diamond Clusters Using Atomic Force Microscopy", Technical Physics Letters, Jul. 2006, 32(7), 561-563.
Ozawa et al, "Preparation and Behavior of Brownish, Clear Nanodiamond Colloids", May 2007, 19(9), 1201-1206.
Osawa et al, "Recent Progress and Perspectives In Single-Digit Nanodiamond", 16(12), Dec. 2007, 2018-2022.
Xu et al, "Mechanochemical Dispersion of Nanodiamond Aggregates in Aqueous Media", J. Mater. Sci. Technol., 2005, 21(1), 109-112.
Xu et al, "Effect of Sodium Oleate Adsorption on the Colloidal Stability and Zeta Potential of Detonation Synthesized Diamond Particles in Aqueous Solutions", Diamond and Related Materials., 2005, 14, 206-212.
Mochalin, "Manufacturing Nanosized Fenofibrate by Salt Assisted Milling", Pharm. Res., Jun. 2009, 26(6), 1365-1370.

* cited by examiner

DISAGGREGATION OF AGGREGATED NANODIAMOND CLUSTERS

CROSS-REFERENCE TO RELATED APPLICATIONS

This application is the National Stage of International Application No. PCT/US2012/036741, filed May 7, 2012, which claims the benefit of U.S. Provisional Application No. 61/486,513, filed May 16, 2011, the disclosures of which are incorporated herein by reference in their entireties.

GOVERNMENT INTERESTS

This invention was made with government support under a grant from the National Science Foundation, NSF grant CMMI-0927963. The government has certain rights in the invention.

TECHNICAL FIELD

The present invention is directed to methods of disaggregating nanodiamond clusters, especially those clusters typically produced from detonation syntheses, the nanodiamond particles and dispersions produced from these disaggregation processes, and compositions derived from these nanodiamond particles and dispersions.

BACKGROUND

While nanotubes, fullerenes, and graphene form the basis of academic and commercial carbon research, other nanoparticulate forms of carbon, such as nanodiamond powder (ND) produced by detonation synthesis (e.g., detonating oxygen-lean explosives in a closed chamber), remain less understood. Currently, large-scale commercial production of nanodiamonds is established in Russia, China, Japan, and several European countries. The rise of interest in nanodiamond is due to its many unique properties, including: superior hardness and Young's modulus, high electrical resistivity, attractive optical characteristics, excellent chemical stability and biocompatibility, all of which it inherits from bulk diamond and delivers on the nanometer scale, in the form of ~5 nm primary particles with large accessible surfaces bearing a variety of reactive functional groups.

Essentially all existing and future applications of nanodiamonds critically depend on the small particle size (e.g., primary particles having effective diameters of 5-10 nm). They have numerous useful properties and are used in applications ranging from lubricants to drug delivery. However, aggregation of nanodiamond particles is limiting wider use of this important carbon nanomaterial, because most applications require single separated particles. As compared to other nanomaterials, the detonation nanodiamonds have an unusually strong tendency to aggregate, which makes the primary nanodiamond particles very difficult to isolate and keep separated. See, e.g., Kruger, A., et al., Carbon, 2005, 43, 1722-1730. The nature of these nanodiamond aggregates is still not clearly understood. It is hypothesized that the extreme conditions in the detonation wave result in dangling bonds on the surface of nanodiamond particles which, in later stages, when temperature and pressure drop, react and either form strong carbon-carbon covalent interparticle bonds, graphitic shells (which may engulf several nanodiamond primary particles and hold them together in a strongly bonded aggregate) or surface functional groups, which can also cause aggregation via hydrogen bond formation or dipole-dipole and weak Van der Waals interactions between the functional groups on adjacent nanodiamond particles. A. Krueger et al., Carbon, 2005, 43, 1722-1730 have proposed a hierarchical model of the nanodiamond aggregates, subdividing them into agglomerates (20-30 nm), intermediate aggregates (2-3 nm), and core aggregates (100-200 nm). While agglomerates and intermediate aggregates can be disintegrated by mild or powerful sonication, the core aggregates, according to Krueger et al., are very strong and cannot be broken up by any conventional mechanical, ultrasound, or surfactant-assisted techniques. For the core nanodiamond aggregates, a model was proposed in which primary nanodiamond particles are embedded into an amorphous and graphitic carbon matrix holding them together.

With ongoing research and conflicting points of view on the nature of the nanodiamond aggregates, the ultimate goal, however, still remains unchanged: to produce the smallest possible nanodiamond particles and keep them separated. As of now, several techniques are known for the disintegration of nanodiamond aggregates. None but the most aggressive have been successful in providing nanodiamond particles/aggregates having effective diameters less than about 40 nm, and these aggressive methods provide particles with difficult to remove impurities. Additionally, dispersion of the resulting nanoparticulate forms result in large aggregates, in some cases larger than the original aggregated nanodiamond clusters. See, e.g., Xu, K., et al., Solid State Phys., 2004, 46, 633-4 and Xu, X. Y., et al., J. Solid State Chem., 2005, 178, 688-693. Such methods include, for example, gas or liquid phase oxidations (see, e.g., Pichot, V., et al., Diamond and Relat. Mater., 2008, 17, 13-22; Osswald, S., et al., J. Am. Chem. Soc., 2006, 128, 11635-11642; and Xu, K., et al., Solid State Phys., 2004, 46, 633-4), high dynamic pressure pulses (see, e.g., Vul, A. Y., et al., Tech. Phys. Left., 2006, 32, 561-3), or by mechanochemical means, optionally supplemented by high power sonication (see., e.g., Osawa, E., Ed. Springer: New York, 2010; pp 1-33; Ozawa, M., et al., Adv. Mater., 2007, 19, 1201-6; Osawa, E., Diamond and Relat. Mater., 2007, 16, 2018-2022; Xu, X. Y., et al., J. Mater. Sci. Technol., 2005, 21, 109-112; Xu, Y. Y., et al., Diamond and Relat. Mater., 2005, 14, 206-212; Mochalin, V. N., et al., Pharm. Res., 2009, 26, 1365-1370;). In the method of Ozawa, M., et al., Adv. Mater., 2007, 19, 1201-6, called bead-assisted sonic disintegration (BASD), high power sonication of a nanodiamond slurry is combined with milling using zirconia microbeads. BASD resulted in a remarkable decrease in the particle size: nanodiamond particles smaller than 10 nm were produced within 2 hours of sonication. However, zirconia contamination left in the nanodiamonds after either milling or BASD, caused by the attriting nanodiamonds, was very difficult to remove as zirconia is highly resistant to most acids/bases, affecting biomedical and other applications of the nanodiamonds.

Consequently, literature shows that, of the well documented techniques, only zirconia microbeads-assisted wet milling and BASD are currently capable of breaking the core nanodiamond aggregates and producing stable suspensions consisting of primary nanodiamond particles. However, contamination of nanodiamonds with difficult-to-remove zirconia, the high cost of zirconia microbeads, and nanodiamond amorphization (or even graphitization) in the course of milling are major drawbacks of the microbeads-assisted milling.

There still is a need for a simple and cost effective approach to disaggregating aggregated nanodiamond clusters for the mass production of disaggregated nanodiamond powders and colloids.

SUMMARY

This invention relates to methods of producing disaggregated nanodiamond powders which are substantially free of metal or metalloid contaminants, and which can be used as free flowing powders or can form colloidal dispersions.

Various embodiments of this invention provide methods of disaggregating nanodiamond clusters combining the aggregated nanodiamond clusters, comprising nanodiamonds and having a mean effective diameter, with solid disaggregating agent having a Mohs hardness less than the Mohs hardness of the nanodiamonds; and milling said combination in a mill having a plurality of milling bodies for a time sufficient to produce a nanodiamond particulate form having a mean effective diameter less than the mean effective diameter of the initial aggregated diamond clusters.

In certain embodiments, the aggregated nanodiamond clusters are those clusters resulting from a detonation process. In separate embodiments, the milling bodies and the disaggregating agent each have a Mohs hardness less than 10. In some embodiments, the disaggregating agent is an organic compound such as sugar, organic acid, or organic salt (for example, sucrose) and in other cases, the disaggregating agent is an inorganic salt (e.g., sodium chloride).

In some embodiments, the solid disaggregating agent is present as a slurry.

Some embodiments further provide a method further comprising separating said final nanodiamond particulate form from at least a portion of the disaggregating agent. Still further embodiments provide that the resulting nanodiamond particulate form is dispersed in a solvent.

Still other embodiments provide compositions, including solids and colloidal dispersions, deriving from the methods described herein.

BRIEF DESCRIPTION OF THE DRAWINGS

The following figures are presented as illustrative examples, and should not be considered to limit the scope of the invention in any way.

FIG. 1A is a representation of a milling chamber filled with stainless steel balls, nanodiamonds, and salt. FIG. 1B is a schematic cartoon illustrating a disaggregation process.

FIG. 2A illustrates the data for a dispersion produced using NaCl as the disaggregating agent and FIG. 2B illustrates the data for a dispersion produced using sucrose as the disaggregating agent. In each case, the particles were re-disbursed at pH=11. Solid lines of the pictographs represent the distribution of particle sizes before disaggregating; dashed lines represent particle size distributions after. Inset in each figure is a visual depiction of the respective dispersion.

FIG. 5B is an enlargement of the boxed region shown in FIG. 5A. FIG. 5C and FIG. 5D provide 3-D reconstructions of electron tomographs of as-received and disaggregated nanodiamonds, respectively, on a lacey carbon support.

DETAILED DESCRIPTION OF ILLUSTRATIVE EMBODIMENTS

Figure 1:
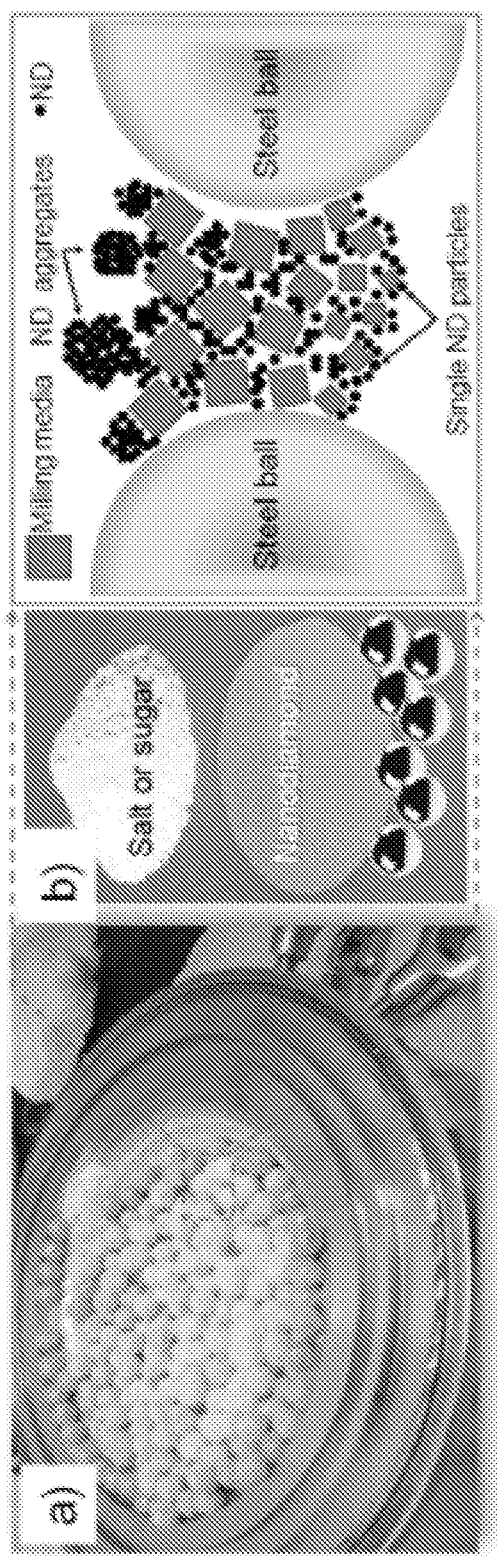
FIG. 1 illustrates the concepts presented herein of the disaggregation process, using salt, sugar, and steel balls as exemplary materials.

This present invention relates to methods of producing disaggregated nanodiamond powders which are free of metal or metalloid contaminants, and which can be used as free flowing powders or can form colloidal dispersions.

The invention is directed to methods of disaggregating nanodiamond clusters, especially those clusters typically produced from detonation syntheses, the nanodiamond particles and dispersions produced from these disaggregation processes, and compositions derived from these nanodiamond particles and dispersions. In specific exemplary embodiments, the present invention teaches dry media assisted milling as a novel, simple, inexpensive, and efficient alternative to the current ways of disaggregating nanodiamond clusters. In certain other embodiments, the technique uses water soluble non-toxic and non-contaminating crystalline compounds such as sodium chloride or sucrose. When milling is complete, the media can be easily removed from the product by simple water rinsing, which provides a remarkable advantage compared to milling with any kind of ceramic microbeads. Using the dry media assisted milling with subsequent pH adjustment, it is possible to produce stable aqueous nanodiamond colloidal solutions with particles<10 nm in diameter, corresponding to 1-2 primary nanodiamond particles.

The present invention may be understood more readily by reference to the following detailed description taken in connection with the accompanying Tables and Figures, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to the method of preparing articles and to the resulting, corresponding physical articles themselves, as well as the referenced and readily apparent applications for such articles.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When values are expressed as approximations by use of the antecedent "about," it will be understood that the particular value forms another embodiment. In general, use of the term "about" indicates approximations that can vary depending on the desired properties sought to be obtained by the disclosed subject matter and is to be interpreted in the specific context in which it is used, based on its function, and the person skilled in the art will be able to interpret it as such. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include each and every value within that range.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Finally, while an embodiment may be described as part of a series of steps or part of a more general composition or structure, each said embodiment may also be considered an independent embodiment in itself.

Certain embodiments of the present invention provide methods of disaggregating nanodiamond clusters comprising combining the aggregated nanodiamond clusters, comprising nanodiamonds and having a mean effective diameter, with solid disaggregating agent having a Mohs hardness less than the Mohs hardness of the nanodiamonds; and milling said combination in a mill having a plurality of milling bodies for a time sufficient to produce a nanodiamond particulate form having a mean effective diameter less than the mean effective diameter of the initial aggregated diamond clusters.

Other embodiments further comprise separating said nanodiamond particles from the disaggregating agent, preferably by dissolving the disaggregating agent in a solvent which dissolves the disaggregating agent preferentially to that of the nanodiamond particles.

The resulting disaggregated nanodiamond powders, which are free of metal or metalloid contaminants, can be used as free flowing powders or can form colloidal dispersions in a number of applications.

As used herein, the term "aggregated nanodiamond clusters" refer to those nanodiamond aggregates comprising agglomerates, intermediate aggregates, core aggregates, and/or mixtures thereof, separate embodiments comprising about 10, 20, 30, 40, 50, 100, or about 1000 or more primary nanodiamond particles. Agglomerates comprising nanodiamond particles found in nanoparticulate form, said particles having a mean particle size within the ranges specified below, should be understood to fall within the scope of the present invention, regardless of whether the agglomerates exceed 1000 nm in size. As described in the Background section of this disclosure, core aggregates resist disaggregation into primary particles by most traditional methods; the methods described herein are especially useful in disaggregating these aggregates. Typically, this term refers to those aggregated nanodiamond clusters which result from a detonation process—so-called detonation nanodiamonds ("NDs"). Such nanodiamonds exhibit the same hardness characteristics as generally attributable to macro-scale diamonds, making their disaggregation especially problematic.

Throughout this specification, unless the context requires otherwise, the term "nanoparticulate form" includes nanoparticle compositions, wherein the composition comprises primary nanodiamond particles having an average particle size smaller than about 10 nm, as well as agglomerates, intermediate aggregates, and core aggregates thereof.

As used herein, the terms "disintegrating," "disaggregating," and "de-agglomerating" used in the context of aggregated nanodiamond clusters refer to the breaking apart of said aggregate clusters into smaller clusters (i.e., containing fewer primary particles) down to and including individual primary nanodiamond particles.

In one embodiment, the aggregated nanodiamond clusters are placed in a media milling device, along with a disaggregating agent and a plurality of milling bodies (milling media, see below) in suitable proportions, that is mechanically agitated (i.e., with or without stirring) for a predetermined period of time at a predetermined intensity of agitation. Typically, a milling apparatus is used to impart motion to the milling bodies by the external application of agitation, whereby various translational, rotational or inversion motions or combinations thereof are applied to the milling chamber and its contents, or by the internal application of agitation through a rotating shaft terminating in a blade, propeller, impeller or paddle or by a combination of both actions. Attritor mills, gravity-dependent-type ball mills, high energy ball mills, planetary mills, tower mills, uniball mills, or vibratory mills may also be used for this purpose. Preferred mills for the process are attritor mills that have a plurality of small solid balls as the grinding media, sized in the range of about 0.2 mm to about 20 mm in diameter, preferably in the range of about 2 to about 15 mm, in the range of about 3 to about 10 mm, or in the range of about 3 mm to about 6 mm in diameter.

It will be appreciated that milling in accordance with the methods of the invention may also be achieved by any suitable means other than ball milling. For example, milling may also be achieved using jet mills, rod mills, roller mills or crusher mills.

The ball to powder ratio and the speed of the mill are two important parameters that determine the energy delivered to the powder in the milling process. Preferably about a 10:1 to about 30:1 weight ratio of ball to powder is used and most preferably about a 20:1 ratio is used. The mill is generally run at about 100 to about 500 rpms. In the mill used in the experiments described herein, the disaggregation efficiency was lower for the speeds higher than 500 rpm.

It should be appreciated that use of the term "milling" or "milling media" typically are used herein for convenience to describe processes or materials used to disaggregate the nanodiamond clusters. While the term "milling" has been used to describe a process whereby the particle size of the target materials is reduced, for example from millimeter to micron or nanometer scale, it should not be construed as carrying this inherent meaning herein. That is, there is no evidence, nor is any implied, that the processes described herein have any effect on the size of the primary particle sizes of the nanodiamonds themselves, which are typically on the order of about 3 nm to about 10 nm as produced. Instead, as used herein, the term "milling" refers to a process involving the transfer of energy from the so-called milling media to the aggregated nanodiamond clusters by way of the disaggregating agent.

Having said this, the milling media may be ceramic, glass, polymer, or metal, preferably carbon or stainless steel or ceramic balls. In each case, the milling bodies have sufficient hardness and resistance to fracture to enable them to avoid being chipped or crushed during milling, abrasion-resistance to minimize attrition resulting in contamination of the product, and also having sufficiently high density. Suitable densities for milling media can range from about 1 to 15 g/cm$^3$.

In various separate embodiments, the milling bodies have Mohs hardness less than those of the nanodiamond clusters or particles (estimated to be ca. 10) and in some cases significantly so—for example, in separate embodiments, less than about 8, less than about 7, less than about 6, less than about 5, or less than about 4 Mohs hardness units, relative to the nanodiamonds. Likewise, the hardness of the disaggregating agent may be less than about 7, less than about 6, less than about 5, less than about 4, less than about 3.5, less than about 3, less than about 2.5, or even less than about 2 Mohs hardness units, relative to the nanodiamonds. It is preferred that the hardness of the crystalline disaggregating agent be less than that of the milling media, so as to minimize the attrition of, and so decontamination by, the latter.

The milling bodies are desirably provided in the form of bodies which may have any of a variety of smooth, regular shapes, flat or curved surfaces, and lacking sharp or raised edges. For example, suitable milling bodies can be in the form of bodies having ellipsoidal, ovoid, spherical or right cylindrical shapes. Preferably, the milling bodies are provided in the form of one or more of beads, balls, spheres, rods, right cylinders, drums or radius-end right cylinders (i.e., right cylinders having hemispherical bases with the same radius as the cylinder).

Similar processes have been described to produce superfine talc and other soft materials, but the fact that it can be used to disaggregate nanodiamond clusters—wherein the conventional thinking prior to the present invention was that the primary particles were joined together by strong carbon-carbon covalent interparticle bonds—was unexpected and quite surprising, especially given the lack of success by other methods. U.S. Patent Application Ser. No. 2003/0234304 ("the '304 application") describes the use of a milling technology to reduce the particle size of talc and calcium carbonate using sodium chloride as a grinding media. The fact that sodium chloride (Mohs hardness=2.5) could be used to reduce the particle size of talc (Mohs hardness=1) or calcium carbonate (Mohs hardness=3) is not that surprising, given the close or higher hardness numbers of the milling media relative to the target material. In fact, a principle advantage described in the 304 application was said to be the ability of the grinding media to prevent re-agglomeration by cold welding, rather than the attrition itself. And while the '304 application described the separation agent (corresponding to the disaggregating agent in the present disclosure) as "ideally" harder than the target powder, it provided no basis for considering that it would work when the difference in hardness between the separation agent and the target powder was significant (e.g., having a difference in Mohs hardness greater than about 0.5-1), such as described herein. For example, there is nothing in the '304 application to suggest that crystalline sodium chloride (Mohs hardness ca. 2.5) would have any effect on nanodiamond clusters (Mohs hardness of the primary particles ca. 10).

Some embodiments provide that the milling is done in the absence of a liquid, such as water, liquid nitrogen or organic solvents. Throughout this specification, unless the context requires otherwise, the phrase "dry mill" or variations, such as "dry milling", should be understood to refer to milling in at least the substantial absence of liquids. Other embodiments provide that the milling is done in the presence of a liquid acting, for example, as a lubricant or thermal sink. If liquids are present, they are present in such amounts that the contents of the mill retain the characteristics of a paste or slurry. That is, in these latter embodiments, sufficient solid disaggregating agent must remain present to effect the disaggregation of the nanodiamond clusters. In either case, embodiments of the present invention provide that the disaggregating agent is present in an amount sufficient to prevent measurable attrition damage to the solid spheres or measurable contamination of the nanodiamond particles with attrited solid milling spheres.

In separate embodiments, the ratio of nanodiamond clusters to disaggregating agent is in the range of about 1:1 to about 1:50 by weight, preferably in the range of about 1:1 to about 1:25, in the range of about 1:1 to about 1:20, in the range of about 1:1 to about 1:15, in the range of about 1:1 to about 1:10, in the range of about 1:1 to about 1:7, in the range of about 1:1 to about 1:5, or about 1:1.

The disaggregating agents of the present invention may be crystalline or amorphous powders, though crystalline or microcrystalline agents are preferred. They may be inorganic salts or organic compounds, but should be capable of being easily removed after milling. Preferably this removal is achieved by dissolving the disaggregating agent, while leaving behind the nanodiamond particles. The particle or crystal sizes of the disaggregating agents are generally preferred to be on the same size scale as the aggregated nanodiamond clusters (see, e.g., FIG. 1B). For example, initial disaggregating agent crystal or particle sizes may be on the order of microns, which may be reduced during the milling process, thereby maintaining comparable size to the nanodiamond cluster throughout the milling process Preferably, the grinding compound has a low tendency to agglomerate during dry milling. While it is difficult to objectively quantify the tendency to agglomerate during milling, it is possible to obtain a subjective measure by observing the level of "caking" of the grinding compound on the milling bodies and the milling chamber of the media mill as dry milling progresses.

In some embodiments, the disaggregating agent is a crystalline inorganic salt. This crystalline salt may comprise an alkali metal, an alkaline earth, or ammonium salt of bicarbonate, bisulfate, carbonate, halide, hydrogen carbonate, hydrogen sulfate, metabisulfite, nitrate, sulfite, hydroxide, sulfate, or thiosulfate. Non-limiting exemplary crystalline materials suitable for this purpose include those comprising ammonium salts (or salts of volatile amines), for example ammonium bromide, ammonium carbonate, ammonium chloride, methylamine hydrochloride; crystalline hydroxides, hydrogen carbonates, hydrogen carbonates of pharmaceutical acceptable alkali metals, such as but not limited by, sodium, potassium, lithium, calcium, and barium; sodium hydrogen sulfate, sodium hydrogen carbonate, sodium hydroxide; sodium sulfate, sodium chloride, sodium metabisulfite, sodium thiosulfate, Glauber's salt, sodium bisulfate, magnesium sulfate, potassium chloride, sodium carbonate, sodium bicarbonate, potassium carbonate, potassium bicarbonate, potassium bromide, or potash alum.

Preferred embodiments are those wherein the salt is a halide salt, more preferably a chloride salt such as sodium chloride. The sodium chloride may be provided in dendritic, granular, or ordinary cubic form.

In certain preferred embodiments, the disaggregating agent is generally recognized as safe (GRAS) by the pharmaceutical industry. The United States Food and Drug Administration provides relevant guidance and standards in this area.

In other embodiments, the disaggregating agent is a crystalline sugar, organic acid, or organic salt. Non-limiting exemplary crystalline materials suitable for this purpose include those comprising lactose, maltose, sucrose, succinic acid, fumaric acid, maleic acid, tartaric acid, citric acid, pharmaceutically acceptable salt thereof, or mixture thereof. Preferred embodiments of the present invention use crystalline sucrose as the disaggregating agent.

As described above, embodiments provide that the milling is done for a time sufficient to obtain an increased portion of nanodiamond particles after the milling relative to before the milling. Suitable rates of agitation and total milling times are adjusted for the type and size of milling apparatus as well as the milling media, the weight ratio of the substrate aggregated nanodiamond clusters/disaggregating agent(s) to the plurality of milling bodies and other parameters that may be optimized empirically. Such optimization is well within the skill of the ordinary artisan.

Certain embodiments provide that this time is in the range of about 5 minutes to about 600 minutes. More generally, this time may be defined in terms of a range wherein the lower limit is about 5 minutes, about 10 minutes, about 15 minutes, about 20 minutes, about 30 minutes, about 60 minutes, about 90 minutes, about 120 minutes, about 180 minutes, and about 240 minutes and upper level is about 600 minutes, about 500 minutes, about 400 minutes, about 300 minutes, about 270 minutes, about 240 minutes, about 210 minutes, about 180 minutes, about 150 minutes, about 120 minutes, about 90 minutes, about 60 minutes, about 45 minutes, or about 30 minutes, as makes logical sense. Exemplary ranges, then, include about 5 minutes to about 600 minutes, about 5 minutes to about 300 minutes, about 30 minutes to about 300 minutes, etc.

Figure 2:
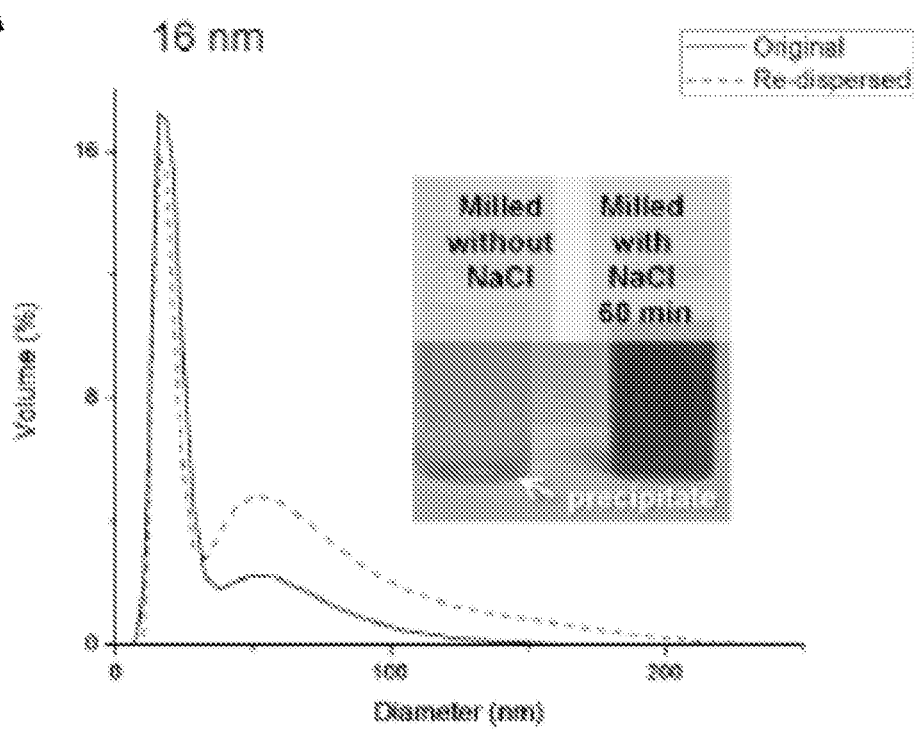
FIG. 2 provides pictographs of particle size distribution of aqueous nanodiamond dispersions made by the present invention.
Figure 2:
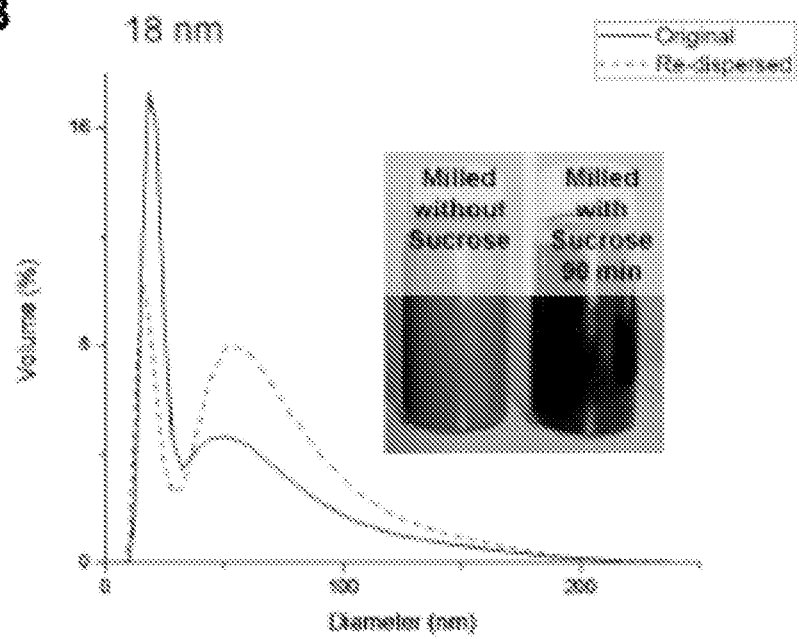

Nanodiamond clusters subjected to 90 minutes of milling using NaCl or sucrose after pH adjustment have both been shown to form stable dark translucent colloidal solutions with particle diameter maxima at 16-18 nm (FIG. 2A, B). The dark translucent appearance of colloidal solutions appears to be typical for single digit nanodiamond particles, suggesting that large aggregates that scatter light were eliminated in this milling regime. The dark color of single digit nanodiamond colloidal solutions is not yet explained (see Example 3).

Figure 3:
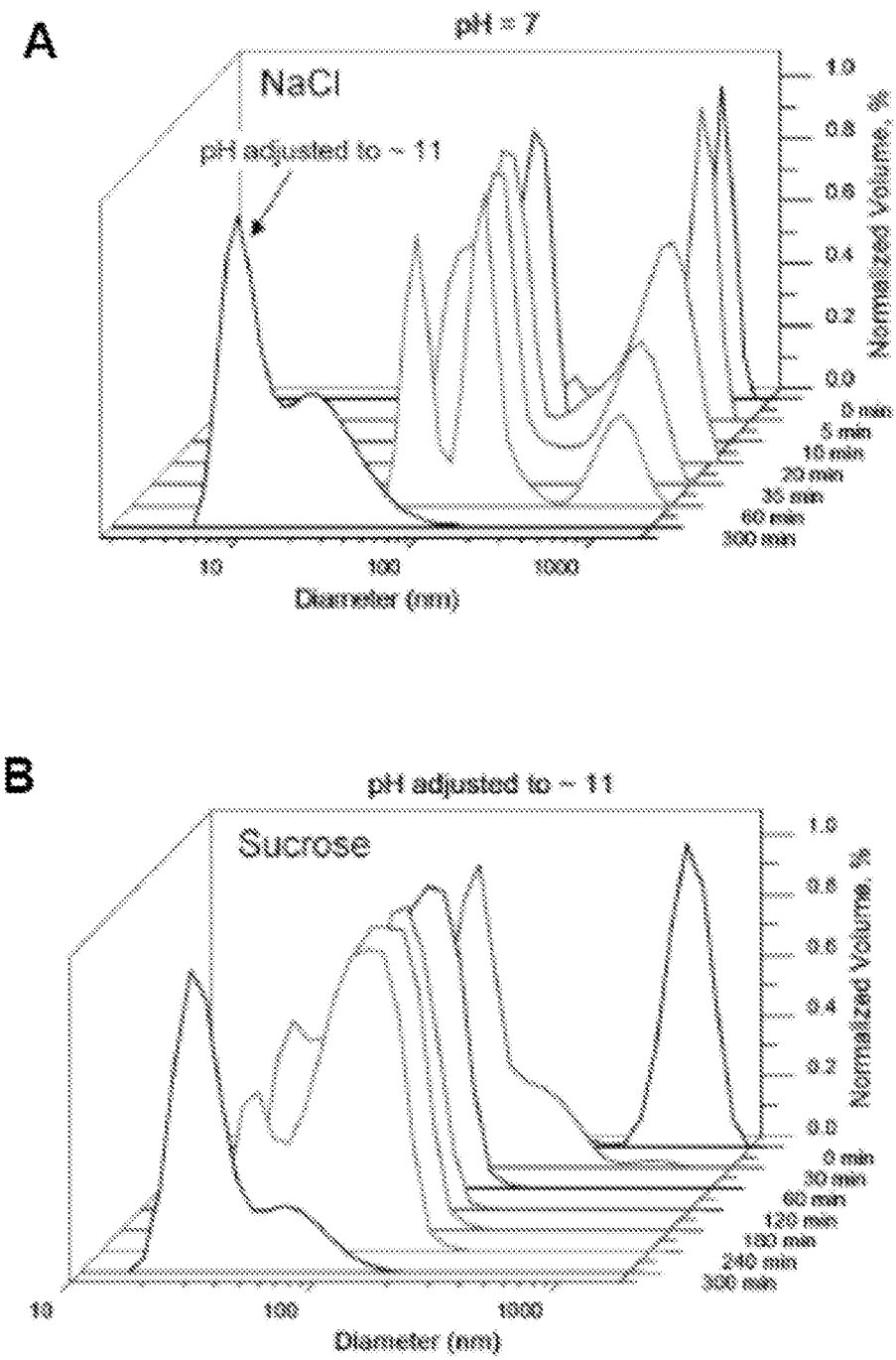
FIG. 3 provides overlapping particle size distributions of disaggregated nanodiamond clusters as a function of milling time for NaCl (FIG. 3A) and sucrose (FIG. 3B).

Exemplary milling kinetics data are presented in FIG. 3A and FIG. 3B. In the beginning, the particle size distribution (PSD) of as-received nanodiamond clusters dispersed in water is centered at about 1000 nm. After only 5 min of salt assisted milling, smaller particles (peak at 150-200 nm) appear in the PSD, while the peak at 1000 nm decreases in intensity (FIG. 3A). Longer milling times result in a further decrease in the number and size of larger aggregates; meanwhile, the smaller particles increase in number and decrease in size. Thus, what was observed in milling is a complex behavior where not only the size, but also the proportion of particles of different size is changing continuously over time. The kinetics is characterized by the change in polydispersity of nanodiamonds, the appearance of shoulder peaks in the PSD, the production of intermediate fractions of particles (an intermediate third peak seen at 35 and 60 min in FIG. 3A), and the subsequent transformation and merger of the fractions with each other. After 5 h of milling and adjusting pH to ~11, the majority of particles is small (~10 nm in diameter) with a small tail extending up to ~100 nm (FIG. 3A).

In separate embodiments, the nanodiamond particulate forms after milling have effective diameters of less than about 50 nm, less than about 40 nm, less than about 30 nm, and less than about 20 nm. In still further embodiments, the portion of nanodiamond particulate forms after milling having diameters less than each of these effective diameters is greater than about 50 vol % of the final nanodiamond content as measured by light scattering techniques. Still additional embodiments provide that the portion of nanodiamond particles after milling having diameters less than each of these effective diameters is greater than about 55, greater than about 60, greater than about 65, greater than about 70, greater than about 75, greater than about 80, greater than about 85, greater than about 90, or greater than about 95 vol % of the final nanodiamond content as measured by light scattering techniques.

Stated differently, in but one series of embodiments, the portion of nanodiamond particles after milling having effective diameters less than 40 nm is greater than about 50, greater than about 55, greater than about 60, greater than about 65, greater than about 70, greater than about 75, greater than about 80, greater than about 85, greater than about 90, or greater than about 95 vol % of the final nanodiamond content as measured by light scattering techniques. In a second series of embodiments, the portion of nanodiamond particles after milling having diameters less than 20 nm is greater than about 50, greater than about 55, greater than about 60, greater than about 65, greater than about 70, greater than about 75, greater than about 80, greater than about 85, greater than about 90, or greater than about 95 vol % of the final nanodiamond content as measured by light scattering techniques.

As used herein, the term "mean particle size" is defined as equivalent spherical diameter as determined by laser light diffraction scattering. Also, because the aggregate nanodiamond clusters, including those of 1-3 primary nanodiamond particles, may be irregular in shape, it is necessary to characterize them not by measurement of an actual size such as thickness or length, but by measurement of a property of the particles which is related to the sample property possessed by a theoretical spherical particle. The particles are thus allocated an "equivalent spherical diameter".

The values found from characterizing a large number of "unknown" particles can be plotted frequency vs. diameter or in other methods weight vs. diameter, usually adopting percentage undersize values for frequency or weight. This gives a characteristic curve representing size distribution of the sample, i.e., cumulative percentage undersize distribution curve. Values from this can be read off directly or plotted on log-probability paper to give an appropriate straight line. The mean equivalent spherical volume diameter is the 50% undersize value.

As used herein, particle size refers to a number average particle size as measured by conventional particle size measuring techniques well known to those skilled in the art, such as sedimentation field flow fractionation, photon correlation spectroscopy, or disk centrifugation. By "an effective average particle size of less than about 40 nm" it is meant that at least 90% of the particles have a number average particle size of less than about 40 nm when measured by the above-noted techniques.

As used herein, the terms "effective diameter" or "effective mean particle diameter" is defined as the diameter or mean diameter of the smallest circular hole through which a particle can pass freely. For example, the effective mean particle diameter of a spherical particle corresponds to the mean particle diameter and the effective mean particle diameter of an ellipsoidal particle corresponds to the mean length of the longest minor axis.

Figure 5:
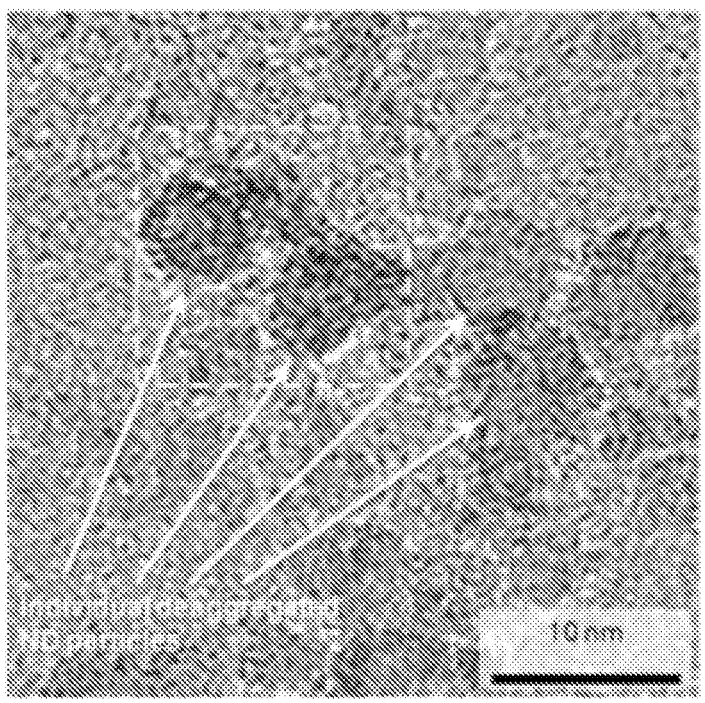
FIG. 5 provides low resolution (FIG. 5A) and high resolution (FIG. 5B) TEM images of nanodiamonds disaggregated with NaCl for 60 minutes.
Figure 5:
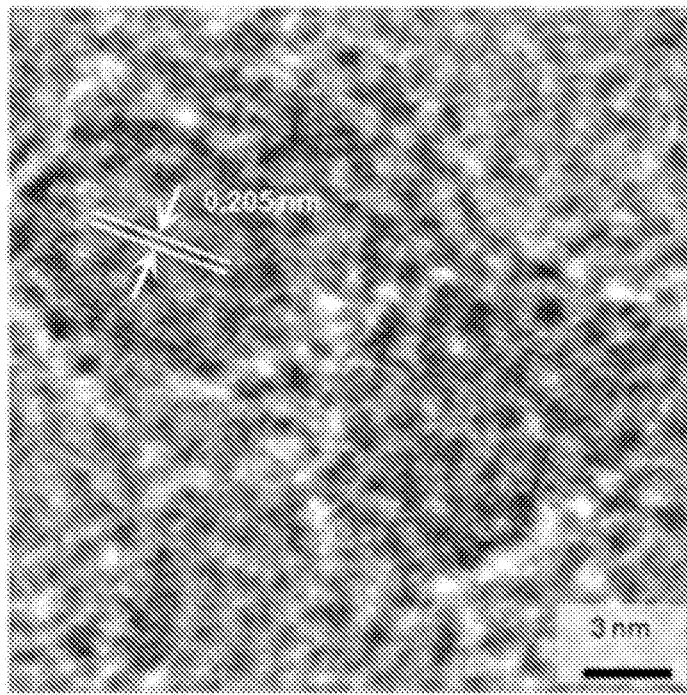
Figure 5:
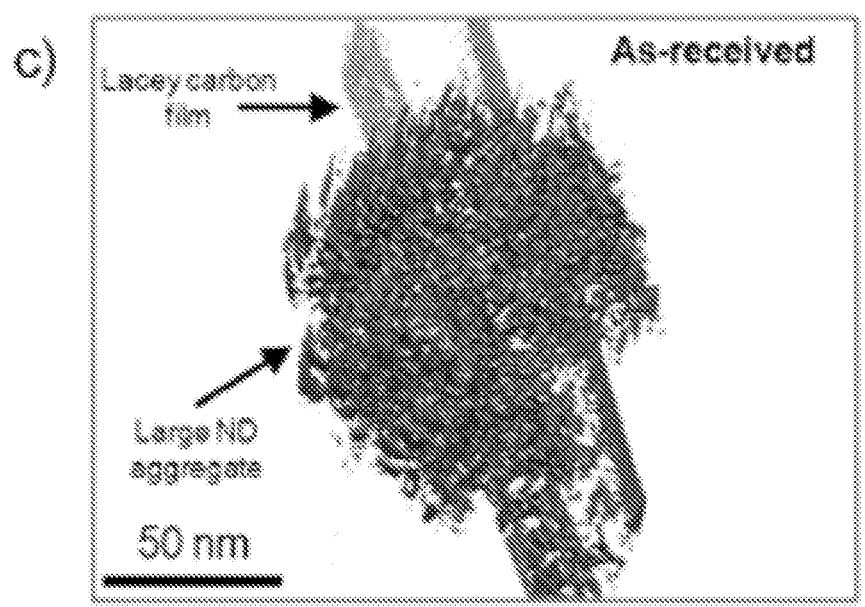
Figure 5:
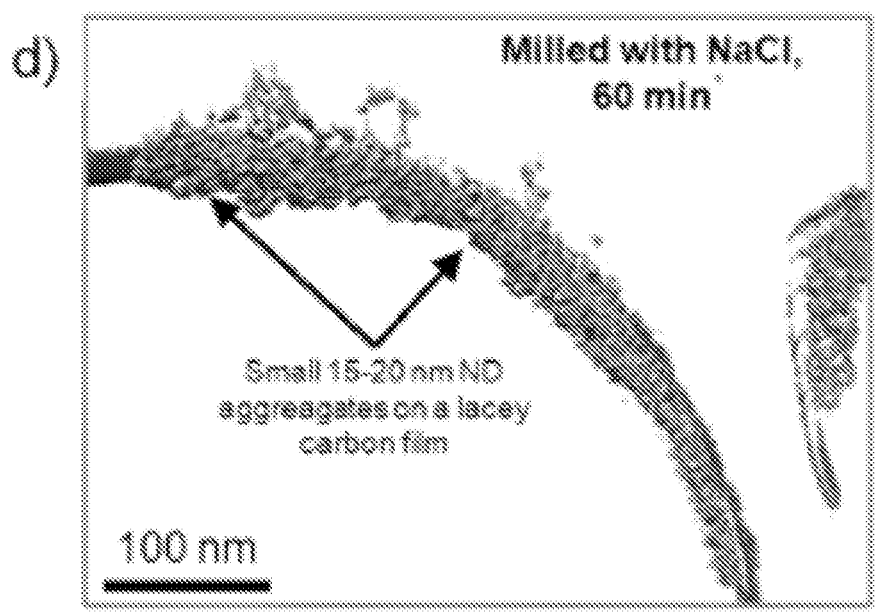
Figure 6:
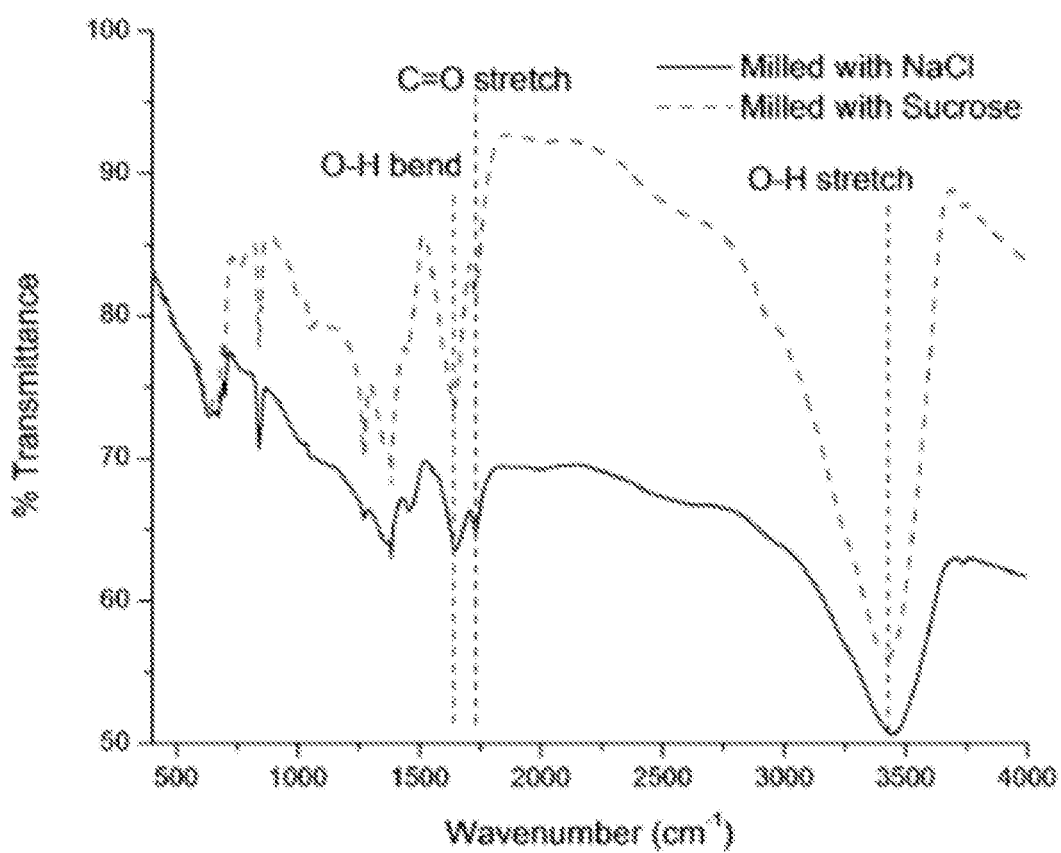
FIG. 6 present FTIR spectra recorded for NaCl- and sucrose-disaggregated nanodiamond powders immediately after milling, before any rinsing. Solid line is spectrum of NaCl-disaggregated powder. Dashed lines is spectrum of sucrose-disaggregated powder.

TEM studies confirm the disaggregation of nanodiamond by milling (FIG. 5). High resolution TEM micrographs of samples of nanodiamond clusters disaggregated by sodium chloride show separate nanodiamonds particles lying close to each other on an amorphous carbon film support (FIG. 5A, B). This surface clustering of nanodiamonds particles is due to the surface tension of water upon drying and is quite different in appearance from the aggregates observed in as-received, non-milled material. The difference is even more emphasized in the 3-D reconstructed TEM electron tomograms shown in FIG. 5C, D. While the as-received nanodiamond typically forms large, dense, 3-D aggregates of hundreds of nanometers in size, milled material shows only small 15-20 nm nanodiamond particles uniformly seeded on the edges of the film after drying (FIG. 5D).

As discussed above, additional embodiments of the present invention include those further comprising separating said nanodiamond particles from at least a portion of the disaggregating agent, preferably all of the disaggregating agent. In these circumstances, the method of the present invention may involve separation of at least a portion of the disaggregating agent(s) from the nanodiamonds in nanoparticulate form by techniques including but not limited to electrostatic separation, magnetic separation, centrifugation (density separation with or without a dispersing media), hydrodynamic separation, froth flotation.

Preferably, the step of removing at least a portion of the disaggregating agent(s) from the nanodiamonds in nanoparticulate form may be performed through means such as selective dissolution or washing, by dissolving the disaggregating agent in a solvent which dissolves the disaggregating agent preferentially to that of the nanodiamond particles. Appropriate solvents may be acid, alkaline or neutral aqueous solutions, or an organic solvent (e.g., alcohol). Any portion of the disaggregating agent(s) may be removed, including but not limited to 10%, 25%, 50%, 75%, or substantially all of the disaggregating agent(s).

While to this point, the invention has been described in terms of methods of disaggregating nanodiamond clusters, it should be appreciated that compositions comprising the resulting nanodiamond particles (either as dry powders or liquid or colloidal dispersions) are also deemed within the scope of the present invention, as are downstream devices and means of treatment including those compositions. For example, pharmaceutical compositions comprising the nanodiamond particles derived from the inventive processes are considered within the scope of the invention, as are electronic or thermally conductive devices which may, for example, take advantage of an electrical behavior or thermal conductivity of the nanodiamond and/or nanodiamond derivative particles (e.g., supercapacitive behavior of alliform carbon). Additionally, any articles resulting from the downstream processing of the nanodiamonds (e.g., annealing) may be seen as within the scope of the present invention.

In still further embodiments, the present invention provides methods for producing a composition comprising substantially mono-modal primary nanodiamond particles comprising: combining aggregated nanodiamond clusters comprising nanodiamonds and having a mean effective diameter with solid disaggregating agent, with solid disaggregating agent having a Mohs hardness less than the Mohs hardness of the nanodiamond particles; and milling the combination in a mill comprising a plurality of solid bodies for a time sufficient to obtain a portion of primary nanodiamond particles having effective diameters less than 40 nm, wherein the portion of primary nanodiamond particles in the combined mixture after milling is greater than the portion of primary nanodiamond particles in the combined mixture before milling.

The disaggregated nanodiamond compositions produced by the methods described herein can be dried and re-dispersed again producing suspensions with same small particles. Additional embodiments include those further comprising separating said nanodiamond particles from the disaggregating agent and re-dispersing the nanodiamond particles in a solvent, preferably an aqueous solvent, i.e., water. In other embodiments the dispersion is adjusted to be made acidic or basic, preferably to made to be basic—in the case of water, the this means adjusting the pH to be between about 1 and about 13, though preferably greater than about 6, about 6.5, or about 7. In other embodiments, dispersing agents may be used.

Figure 4:
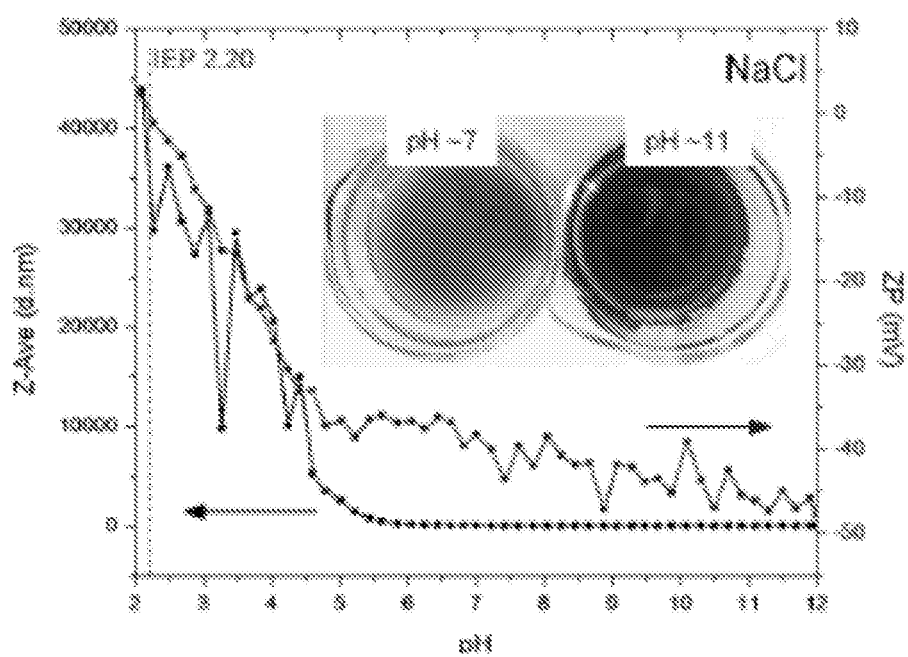
FIG. 4 provides particle size and zeta potential as a function of pH of aqueous milled (5 hours) nanodiamond clusters using NaCl (FIG. 4A) and sucrose (FIG. 4B). Inset in FIG. 4A are representations of NaCl milled nanodiamond (90 minutes) colloidal solutions before and after the addition of 0.5 mL of 0.1 M NaOH to adjust to pH ca. 11.
Figure 4:
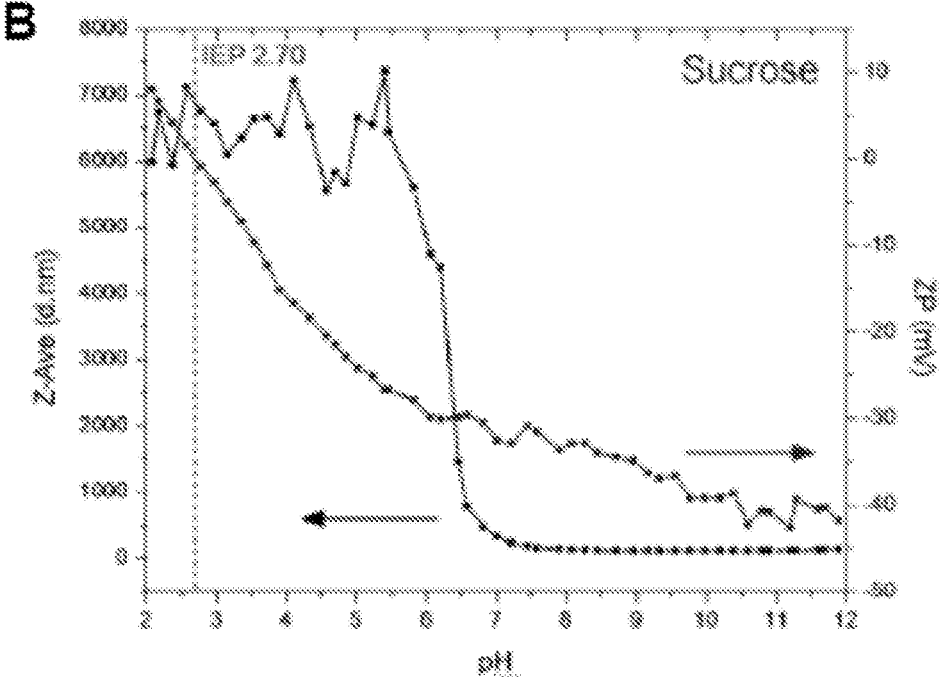

The nanodiamond particles provided by the methods described herein are further characterized by an isoelectric point of less than about 7. FIG. 4A, B illustrate the size and zeta potential of the particles as functions of pH. Zeta-potentials were found to be negative and decreasing from −(30-35) mV at pH 7 to −(40-45) mV at pH 12. As a result, the particle size was minimal in this pH range. Based on the titration data, the pH of aqueous suspensions of disaggregated nanodiamonds was adjusted to 11.4 by adding 5-7 drops of 0.1 M NaOH to 10 mL of the nanodiamond suspension. Combined with the disaggregation, pH adjustment led to a substantial reduction in the amount of larger aggregates (FIG. 4B) as compared to non-adjusted suspensions (FIG. 4A). The pH stability range for the nanodiamond particles disaggregated using NaCl (FIG. 4A) was larger and the isoelectric point was achieved in a more acidic environment as compared to the nanodiamond particles disaggregated using sucrose (FIG. 4B). Without being bound by any particular theory, this observation may be rationalized by the different changes in the surface chemistry of nanodiamonds caused by the two different milling media.

In separate embodiments, the pH of the dispersions is adjusted to a range having a lower end value of about 6, about 6.5, about 7, about 7.5, about 8, about 8.5, about 9, about 9.5, about 10, about 10.5, and about 11 and an upper end value of about 13, about 12.5, about 12, about 11.5, about 11, about 10.5, about 10, about 9.5, about 9, about 8.5, or about 8 pH units. Exemplary ranges include those wherein the pH range is from about 6.5 to about 14, from about 7 to about 13, from about 8 to about 12, from about 9 to about 12, from about 10 to about 12, and about 10.5 to about 11.5, or where the pH is about 11.

Again, the dispersions produced by these methods are also considered within the scope of the present invention. In preferred embodiments, these dispersions are colloidal dispersions which are substantially free of aggregates having an effective diameter greater than about 250, about 200, about 100 nm, or about 60 nm. While the term "substantially free" is understood by the skilled artisan to mean, in some embodiments, the term "substantially free of aggregates" may mean having less than 10 vol %, less than 5 vol %, less than 2 vol %, or less than 1 vol % of said aggregates, relative to the total solid volume of the dispersion.

While the text of this disclosure focuses on aggregated and disaggregated nanodiamonds, it should be appreciated that the same principles and considerations apply to other hard materials—for example, alliform carbon (described more fully in co-pending application titled "Supercapacitors Based On Alliform Carbon," Applicants' Ref DXU-0349), carbon nano-onions, nanotubes, fullerenes, carbon black, and other nano-dimensioned ceramics, and metal particles—where the processing results in disaggregation of aggregated material clusters with milling media without appreciable reduction in size of the much harder primary particles—e.g., less than 10%, less than about 5%, or less than about 1% reduction of the original primary particle size—or change in surface roughness of the primary particles.

The present invention will now be described with reference to the following non-limiting Examples. The description of the Examples is in no way limiting on the preceding paragraphs of this specification, but is provided for exemplification of the methods and compositions of the invention.

EXAMPLES

Example 1

Materials and Procedures

Nanodiamond powder (UD90 grade) was obtained from Nanoblox, Inc., USA and used without subsequent purification. Sodium chloride and sucrose were purchased from Sigma-Aldrich, USA, with particle sizes of 80 and 72 mesh respectively.

A temperature controlled lab attrition mill with a 110 cm³ milling chamber and stainless steel milling balls, 0.635 cm (¼ inch) in diameter, was designed and manufactured by Union Process, Inc., USA. The vessel was cooled to 0° C. and maintained at this temperature for the course of milling in order to minimize thermal damage of the sample by heat generated due to wear and impact. The mill was loaded with a charge consisting of nanodiamond powder, dry disaggregating agent (sodium chloride or sucrose), and 538.6 g (19 oz) steel milling balls (FIG. 1A). The charge was milled with varying time at 500 rpm and 1:7 nanodiamond:disaggregating agent ratio.

The milled nanodiamond was repeatedly rinsed with de-ionized water in a 500 mL beaker until negative test with 0.1N silver nitrate (when NaCl was used as a disaggregating agent). In the case of sugar, rinsing was performed 6 times in order to assure that the sugar had been completely removed. After the last rinsing, nanodiamonds still partially precipitated from the suspension as its concentration was too high to maintain a stable system. Once the equilibrium was established, the part that remained in the suspension was taken and used for subsequent tests.

Malvern Zetasizer Nano ZS with an MPT-2 autotitrator was used for particle size and zeta-potential vs. pH measurements.

TEM analysis was carried out on a JEOL JEM-2100 microscope with an operating voltage of 200 kV. Samples for TEM were produced by dipping the lacey carbon coated Cu grid into the aqueous nanodiamond colloidal solution and letting it dry in air. This TEM is equipped with a high tilt sample holder allowing tilt angles up to ±60°. Serial EM software was used to record the tilt series and IMOD software was used for reconstruction of tomograms.

Example 2

Results

The results of experiments are described in FIGS. 1-6 and are described throughout this disclosure.

Example 3

Observations on Color

As described above, nanodiamond clusters subjected to 90 minutes of milling using NaCl or sucrose after pH adjustment both form stable dark translucent colloidal solutions with particle diameter maxima at 16-18 nm (FIG. 2A, B). The dark translucent appearance of colloidal solutions appears to be typical for single digit nanodiamond particles, suggesting that large aggregates that scatter light were eliminated in this milling regime. The dark color of single digit nanodiamond colloidal solutions is not yet explained. It has previously been hypothesized to originate from graphitic or amorphous $sp^2$ carbon on the surface of nanodiamonds (e.g., see above). Analysis of milled pH adjusted samples in the present work rules out the latter hypothesis. The small amounts of 0.1 M NaOH used to shift the pH of the milled nanodiamond suspensions cannot induce the conversion of diamond into graphitic or amorphous carbon; nevertheless, the suspension turns from opaque pale brown into translucent dark brown in a matter of seconds upon adding the base (see inset in FIG. 4A). Thus, it appears that the dark brown color of aqueous nanodiamond colloidal solutions is not due to graphitic or amorphous carbon.

Example 4

On Aggregate Equilibrium

An increase in milling time up to 5 h with subsequent pH adjustment results in a further reduction in particle size and an increase of proportion of smaller nanodiamond aggregates with sub-10 nm diameter particles eventually dominating the PSD in the case of NaCl milled pH adjusted colloidal solution (FIG. 3A). This corresponds to 1-2 primary particles given that the diameter of a nanodiamond particle is ~5 nm. However, in these experiments, the PSD of colloidal nanodiamond dispersions never included peaks at 5 nm, which is commonly considered as an indicative of single digit diamond suspension. There could be several reasons why there is no 5 nm particles peak in PSD even after 5 hours of milling. First, the PSD can be affected by a fraction of larger primary nanodiamond particles present in the nanodiamond samples used. The nanodiamonds used in this study contained a fraction of 15-30 nm primary particles which can be detected by TEM, XRD and Raman spectroscopy after burning off smaller nanodiamond particles in air. The presence of the larger primary particles may result in a shift towards larger sizes in the PSD of the milled samples. Second, the nanodiamond aggregates observed after milling could be dynamic in nature, i.e. on one hand, continuously formed due to collisions between few nanodiamond primary particles and held together by the weak interparticle interactions; on the other hand, continuously destroyed due to collisions with other particles and with molecules of the environment. Thus, there is a dynamic equilibrium between the nanodiamond aggregates and primary particles in colloidal solution, similar to that observed for chemical reactions:

$$(ND)_n \leftrightarrows nND \qquad (2)$$

An argument in favor of the dynamic aggregates hypothesis is a large scatter often observed between PSD curves recorded repeatedly (10-20 times) for the same sample.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article.

The disclosures of each patent, patent application, and publication cited or described in this document are hereby incorporated herein by reference, in their entirety.

What is claimed:

1. A method of disaggregating nanodiamond clusters comprising:
    milling aggregated nanodiamond clusters with a plurality of milling bodies and a solid disaggregating agent having a Mohs hardness less than 6 Mohs hardness units, the aggregated nanodiamond clusters comprising nanodiamonds and having an initial mean effective diameter, the milling being done for a time sufficient to produce a nanodiamond particulate form having a mean effective diameter less than the initial mean effective diameter of the aggregated nanodiamond clusters.

2. The method of claim 1 wherein the aggregated nanodiamond clusters are aggregated nanodiamond clusters resulting from a detonation process.

3. The method of claim 1 wherein the milling bodies have a Mohs hardness less than 10.

4. The method of claim 1 wherein the milling bodies comprise ceramic, glass, polymer, or metal.

5. The method of claim 1 wherein said solid disaggregating agent is present as a slurry.

6. The method of claim 1 wherein the milling is done in the presence of a liquid.

7. The method of claim 1 wherein the disaggregating agent is present in an amount sufficient to prevent measurable attrition damage to the milling bodies and/or measurable contamination of the nanodiamond particulate form with said attrition damage.

8. The method of claim 1 wherein the ratio of nanodiamond clusters to disaggregating agent is in the range of 1:1 to 1:50 by weight.

9. The method of claim 1 wherein the disaggregating agent is generally recognized as safe (GRAS) by the pharmaceutical industry.

10. The method of claim 1 wherein the disaggregating agent is a crystalline inorganic salt.

11. The method of claim 10 wherein the crystalline inorganic salt is a crystalline alkali metal or alkaline earth metal halide salt.

12. The method of claim 11 wherein the crystalline inorganic salt is a chloride salt.

13. The method of claim 12 wherein the chloride salt is sodium chloride.

14. The method of claim 1 wherein the disaggregating agent is a crystalline sugar, organic acid, or organic salt.

15. The method of claim 14 wherein the disaggregating agent is a crystalline lactose, maltose, sucrose, succinic acid, fumaric acid, maleic acid, tartaric acid, citric acid, pharmaceutically acceptable salt thereof, or mixture thereof.

16. The method of claim 15 wherein the disaggregating agent is sucrose.

17. The method of claim 1 wherein the time is in the range of 5 minutes to 600 minutes.

18. The method of claim 1 providing a portion of the nanodiamond particulate form having an effective diameter of less than 40 nm.

19. The method of claim 18 wherein the portion of the nanodiamond particulate form having effective diameters less than 40 nm is greater than 50 vol % of the total nanodiamond particulate form content as measured by light scattering techniques.

20. The method of claim 1 further comprising separating the nanodiamond particulate form from at least a portion of the disaggregating agent.

21. The method of claim 20 wherein the separating comprises dissolving at least a portion of the disaggregating agent in a solvent.

22. The method of claim 21 wherein the solvent is aqueous.

23. The method of claim 1, further comprising dispersing the nanodiamond particulate form in a solvent.

24. The method of claim 23 wherein the solvent is aqueous.

25. The method of claim 24 further comprising adjusting the pH of the aqueous solvent to greater than 6.

26. The method of claim 25 wherein the pH is in the range of about 10.5 to about 11.5.

27. The method of claim 1, wherein said solid disaggregating agent has a Mohs hardness less than 5 Mohs hardness units.

28. The method of claim 1, wherein said solid disaggregating agent has a Mohs hardness less than 4 Mohs hardness units.

29. The method of claim 1, wherein said solid disaggregating agent has a Mohs hardness less than 3 Mohs hardness units.

30. The method of claim 1, wherein said solid disaggregating agent has a Mohs hardness less than 2.5 Mohs hardness units.

* * * * *